United States Patent [19]

Brown

[11] 4,262,117

[45] Apr. 14, 1981

[54] CYANOVINYL CYCLOPROPANECARBOXYLIC ACIDS

[75] Inventor: Dale G. Brown, Hopewell, N.J.

[73] Assignee: American Cyanamid Company, Stamford, Conn.

[21] Appl. No.: 58,234

[22] Filed: Jul. 16, 1979

Related U.S. Application Data

[63] Continuation of Ser. No. 937,359, Aug. 28, 1978, abandoned.

[51] Int. Cl.³ .............................................. C07C 121/46
[52] U.S. Cl. ................................ 542/429; 260/465 D; 424/275; 424/282; 424/304
[58] Field of Search .................. 260/465 D; 542/429; 424/304

[56] References Cited

U.S. PATENT DOCUMENTS

| | | | |
|---|---|---|---|
| 3,679,667 | 7/1972 | Fanta | 542/429 |
| 3,723,469 | 3/1973 | Martel | 542/429 |
| 3,786,052 | 1/1974 | Martel | 542/429 |
| 3,890,364 | 6/1975 | Knupfer et al. | 260/465 D |
| 3,997,586 | 12/1976 | Martel | 542/429 |
| 4,003,943 | 1/1977 | Fukunaga | 260/465 D |
| 4,062,968 | 12/1977 | Fujimoto et al. | 424/308 |
| 4,157,447 | 6/1977 | Engel | 260/465 D |

OTHER PUBLICATIONS

Elliott et al., J. Chem. Soc. Perkins (I), 1974, pp. 2470-2474.
Kondo Tet. Letters #48, (1976), pp. 4359-4362.
Matsui et al., Chem. Abst. 59, (1963), col. 11288d,e.
Velluz et al., Chem. Abst. 71, (1969), #60791.

*Primary Examiner*—Arthur P. Demers
*Attorney, Agent, or Firm*—H. G. Jackson

[57] ABSTRACT

The invention relates to novel substituted cyanovinyl cyclopropanecarboxylic acids and method of preparation thereof. The cyanovinyl cyclopropanecarboxylic acids are useful intermediates for the preparation of novel insecticidal-acaricidal pyrethroids.

7 Claims, No Drawings

CYANOVINYL CYCLOPROPANECARBOXYLIC ACIDS

This is a continuation of application Ser. No. 937,359 filed Aug. 28, 1978, now abandoned.

The invention relates to substituted cyanovinyl cyclopropanecarboxylic acids of formula (IV) below:

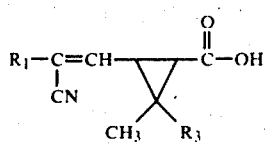

wherein $R_1$ is

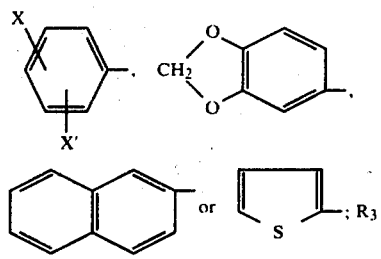

is selected from hydrogen or methyl; and X and X' are each hydrogen, halogen, $C_1$-$C_3$ alkyl, $C_1$-$C_3$ alkoxy or haloalkyl $C_1$-$C_2$.

The compounds represented by formula (IV) above may exist in a number of geometric and optical isomeric forms and mixtures thereof. Those isomers in which the carboxylic acid and the cyanovinyl functions are on the opposite sides of the cyclopropare ring are designated as trans; those in which they are on the same side as designated as cis. In each case these may be separated into (+) and (−) optical isomers by appropriate methods, such as the use of chiral bases in the separation of the carboxylic acids. A further locale for geometrical isomerism is the cyanovinyl function itself. In this case the designation Z is given to those compounds in which the cyano and cyclopropyl substituents are on the same side of the carbon-carbon double bond, whereas the E isomer is that in which the aryl or heterocyclic and the cyclopropyl subsituents are so situated. Thus, the hereinabove defined compounds of formula (IV) may be the cis and trans cyclopropane isomers, the E and Z sidechain olefin isomers, the optical isomers thereof and the isomeric mixtures thereof.

Among the cyanovinyl cyclopropanecarboxylic acids represented by formula (IV) above, a preferred group of compounds are those wherein $R_1$ is selected from

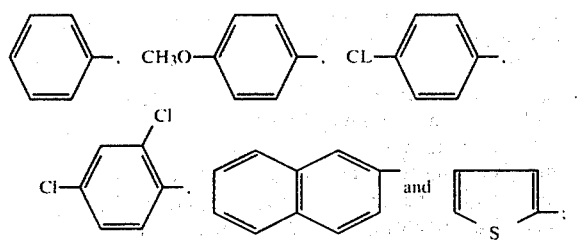

$R_3$ is methyl; the cis and trans cyclopropane isomers, the E and Z side-chain olefin isomers, the optical isomers thereof, and the isomeric mixtures thereof.

The cyanovinyl cyclopropanecarboxylic acids of the invention described and defined by formula (IV) above, are useful and valuable intermediates for the preparation of novel insecticidal and acaricidal pyrethroids of formula (I) as follows:

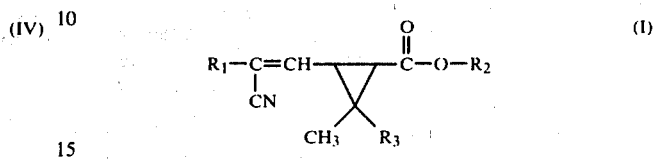

wherein $R_1$ and $R_3$ are as defined above; $R_2$ is a moiety selected from

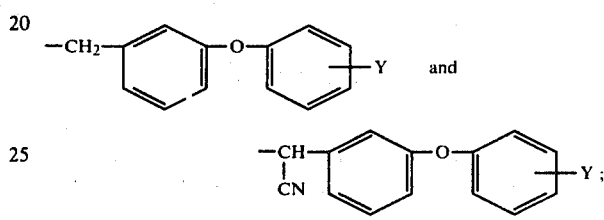

and Y is hydrogen, halogen, methyl or methoxy. When $R_2$ is the moiety: α-cyano-m-phenoxybenzyl, then the compounds of formula (I) possess an additional chiral center. The compounds of formula (I) may be the cis and trans cyclopropane isomers, the E and Z sidechain olefin isomers, the optical isomers thereof and the isomeric mixtures thereof. The insecticidal and acaricidal pyrethroids represented by formula (I) are disclosed and claimed in our co-pending application for United States Letters Patent, Ser. No. 937,360, now abandoned, filed on an even date with this invention.

The novel compounds of the invention represented by formula (IV) may be conveniently prepared by a reaction sequence schematically depicted, and discussed as follows:

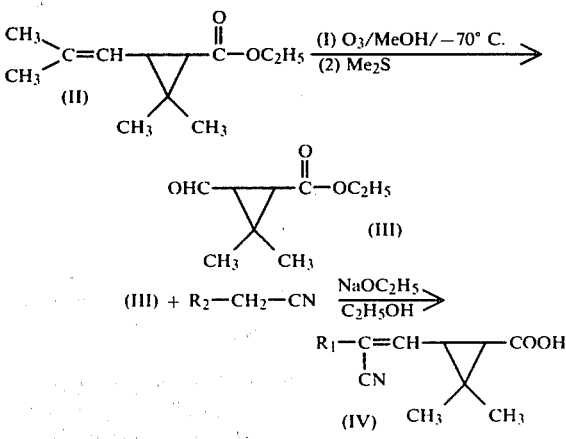

In the above reaction sequence $R_1$ is as hereinabove defined and $R_3$ is represented by methyl; and the thus-obtained compounds of formula (IV) are the cis and trans cyclopropane isomers the E and Z side-chain olefin isomers, the optical isomers thereof, and the isomeric mixtures thereof. Thus, ethyl chrysanthemate (II)

is oxidized with ozone in a methanolic solution at a temperature range of about −50° C. to −70° C., the crude reaction mixture treated with dimethyl sulfide to remove the excess ozone, to afford the corresponding ethyl 3-formyl-2,2-dimethylcyclopropanecarboxylate (III). The above formyl compound is then condensed with a compound of formula $R_1$—$CH_2$—CN in the presence of a base, such as sodium ethoxide and a lower alcohol, such as ethanol, to yield the desired cyanovinyl cyclopropanecarboxylic acid of formula (IV).

As stated above, the formula (IV) cyclopropanecarboxylic acids of the invention are useful and valuable intermediates for the preparation of formula (I) insecticidal and acaricidal pyrethroids.

A formula (I) pyrethroid may conveniently be prepared from a formula (IV) compound as illustrated graphically, and discussed in the following:

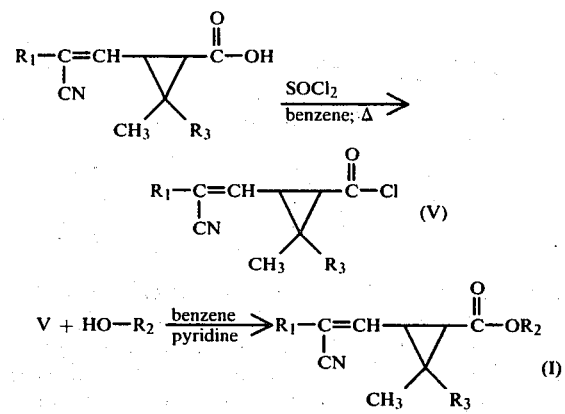

wherein in the above reaction sequence $R_1$ is

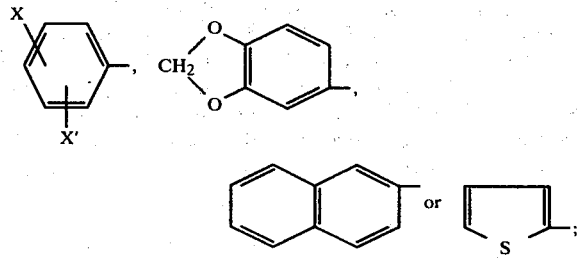

$R_2$ is a moiety selected from

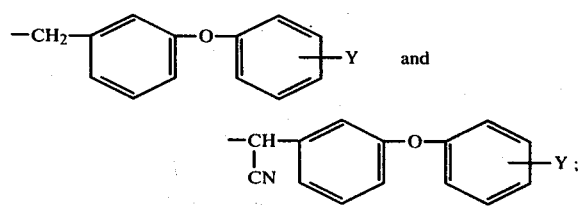

$R_3$ is hydrogen or methyl; X and X' are each selected from hydrogen, halogen, $C_1$-$C_3$ alkyl, $C_1$-$C_3$ alkoxy and haloalkyl $C_1$-$C_2$; Y is selected from hydrogen, halogen, methyl and methoxy; the cis and trans cyclopropane isomers, the E and Z side-chain olefin isomers, the optical isomers thereof, and the isomeric mixtures thereof. Thus, a formula (IV) acid is converted to the corresponding acid chloride (V) with thionyl chloride in an inert aromatic solvent such as benzene, toluene or xylene. The acid chloride (V) is then reacted with an alcohol of formula $R_2$-OH in the presence of an acid acceptor, such as pyridine, in an inert aromatic solvent, such as benzene, toluene or xylene, to afford the desired insecticidal/acaricidyl pyrethroids of formula (I).

Alternatively, formula (I) pyrethroids may be prepared from the cyanovinyl cyclopropanecarboxylic acids (IV) or acid chlorides (V) of the invention via ester forming reactions promoted by phase transfer catalysts. These reactions may be graphically illustrated as follows:

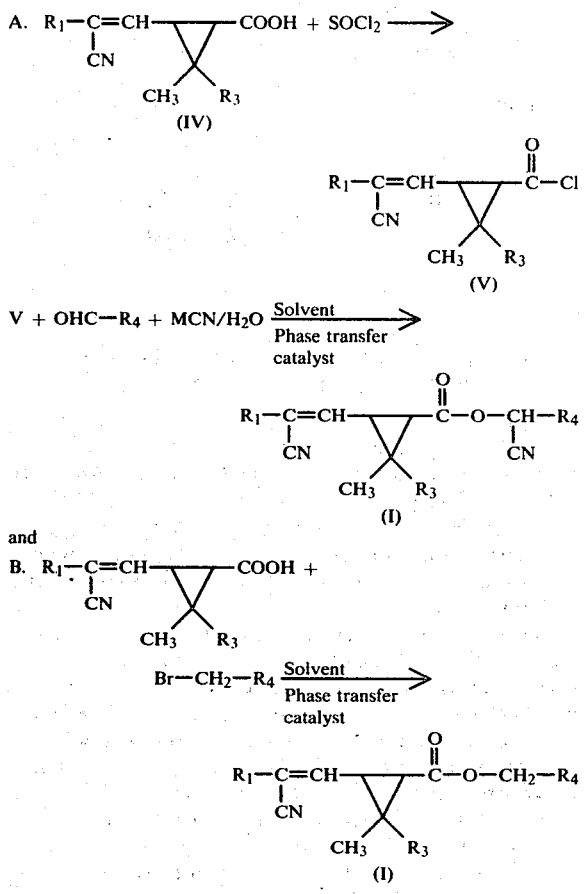

wherein in the above reaction schemes A and B, $R_1$ and $R_3$ are as hereinabove defined; $R_4$ is

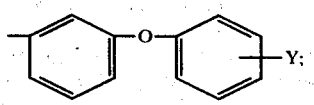

M is sodium or potassium; Y is selected from hydrogen, halogen, methyl or methoxy; the cis and trans cyclopropane isomers, the E and Z side-chain olefin isomers, the optical isomers thereof and the isomeric mixtures thereof.

In the above reactions, the phase transfer catalysts are selected from benzyltriethylammonium chloride, benzyl-tri-n-propylammonium chloride, α-methylbenzyltriethylammonium iodide, tetrabutylammonium chloride and iodide, methyl tricaprylammonium chloride, hexadecyl trimethylammonium bromide, benzyl triphenylphosphonium bromide; crown ethers, such as 18-crown-6, dicyclohexyl-18-crown-6, dibenzo-18-crown-6; and the like. These phase transfer catalysts are utilized in amounts of from 0.1% to 10% molar quantities in the above reactions. Solvents for these reactions are selected from methylene chloride, chloroform, 1,2-dichloroethane, hexane, heptane, cyclohexane, benzene, toluene, xylene, ethyl acetate, and the like.

The above processes, using phase transfer catalysts for the preparation of insecticidal/acaricidal pyrethroids of formula (I) are disclosed and claimed in our co-pending application for United States Letters Patent, Ser. No. 937,361, now abandoned, filed on an even date with this invention.

As stated above, the compounds of the invention represented by formula (IV) are useful and valuable intermediates for the preparation of insecticidal and acaricidal pyrethroids of formula (I). The pyrethroids of formula (I) are eminently suitable for the control of insect pests of agriculturally important crops and for the control of ectoparasites, especially acarina, of domesticated warmblooded animals.

The following non-limiting examples further serve to illustrate the invention.

EXAMPLE 1

Preparation of 3-formyl-2,2-dimethyl-cyclopropanecarboxylic acid ethyl ester

A solution of ethyl chrysanthemate (156.0 g) in absolute methanol (1400 ml) is stirred, cooled to −65° C., and ozone bubbled in at a rate of 1.7 l/min. under 0.56 kg/cm² pressure (the ozone is generated with a Welsbach T-23 ozonator; voltage setting 120 VAC). During the reaction, the temperature range of the reaction mixture fluctuates between −65° C. and −50° C.

The reaction is followed with gas chromagraphy [6′×¼″ glass column, packed with 3% OV-1 on WHP; temperature 130° C.; sample size 0.2λ; flow 45 ml/min He; FID detector] to measure the disappearance of ethyl chrysanthemate. The ozonolysis is stopped after about 6 to 7 hous, when about 5% ethyl chrysanthemate is still present. Methyl sulfide (125 ml) is added over 20 minutes, and the reaction mixture allowed to warm up to room temperature overnight with stirring. Next, the methanol is removed in vacuo at 50°–55° C. The residual oil is diluted with ether, and the ether solution washed with water. The ether layer is dried over magnesium sulfate, filtered, and is then evaporated to yield 131.3 g of title product.

An nmr is run on the product to determine if any acetal which may have been formed during the reaction [multiplet at 3.4δ] is present. If acetal is found in the product, 10% hydrochloric acid (85 ml) is added with stirring followed by the addition of sufficient amount of tetrahydrofuran to obtain a homogeneous solution. The solution is heated at 40°–50° C. for one hour. Water and ether are added, and the aqueous layer extrated with ether. The ether layers are combined, dried over magnesium sulfate and evaporated in vacuo to afford the title product.

EXAMPLE 2

Preparation of (Z)-cis and trans-3-(β-cyanostyryl)-2,2-dimethyl-cyclopropanecarboxylic acid Phenylacetonitrile is added to a stirred solution of sodium ethoxide in absolute ethanol (prepared from 1.1 g sodium and 100 ml of ethanol). Next, a solution of 3-formyl-2,2-dimethyl-cyclopropanecarboxylic acid ethyl ester (8.5 g) in absolute ethanol (15 ml) is added over 5 minutes. The reaction mixture is stirred for 12 hours at room temperature and then heated on a steam bath for 0.5 hour. The alcohol is removed in vacuo, and the residue washed with water (250 ml) and ether (150 ml). The aqueous layer is acidified with concentrated hydrochloric acid. The resulting cream colored slurry is filtered and the isolated product dried. The product is dissolved in ether and precipitated with hexane to afford 6.1 g of white crystals, m.p. 186°–188° C.

By the above procedure, a number of cyclopropanecarboxylic acids are prepared. There are listed in Table I below, together with their melting points.

TABLE I

Substituted cyclopropanecarboxylic acids.

$$R_1-C=CH-\underset{\underset{CH_3 \ CH_3}{\triangle}}{\phantom{X}}-\overset{O}{\underset{\phantom{X}}{C}}-OH$$
$$\phantom{XXXXX}|$$
$$\phantom{XXXX}CN$$

| $R_1$ | m.p. °C. |
|---|---|
| Cl—C₆H₄— | 190–208 |
| CH₃O—C₆H₄— | 188–198 |
| C₆H₅— | 120–142 |
| 3,4-Cl₂—C₆H₃— | 130–145 |
| 2-naphthyl | 217–218 |
| 2-thienyl | 140–143 |
| 3-Cl—C₆H₄— | 125–155 |
| 3,4-methylenedioxyphenyl | 160–180 |
| Br—C₆H₄— | 179–195 |
| 3,4-Cl₂—C₆H₃— | 195–202 |

TABLE I-continued

Substituted cyclopropanecarboxylic acids.

$$R_1-C=CH-\underset{\underset{CH_3 \quad CH_3}{\triangle}}{}-\overset{O}{\underset{}{C}}-OH$$
$$\phantom{R_1-}\underset{CN}{|}$$

| $R_1$ | m.p. °C. |
|---|---|
| 2-Cl-phenyl | * |
| 2,3-diCl-phenyl | 103–112 |
| 4-F-phenyl | 150–164 |
| 4-CH$_3$-phenyl | 164–176 |
| 4-CF$_3$-phenyl | 117–123 |

* = Gum - NMR TMS CDCl$_3$ doublet 6.30 δ and doublet 7.05 δ

EXAMPLE 3

Preparation of 2-Formyl-3-methylcyclopropanecarboxylic acid, ethyl ester

Crotonaldehyde (14.0 g, 0.2 mole) is added dropwise to a gently refluxing solution of tetrahydrothiophene ylid (34.0 g, 0.2 mole) in dry acetone (200 ml). Heating at reflux is continued for about 15 minutes after the addition is completed, then the reaction mixture is concentrated on a rotary evaporator at 50° C. Distillation of this concentrate at reduced pressure affords 15.32 g (49.1%) of title product, a pale yellow oil, b.p. 0.1 mm 44°–45° C. The structure is confirmed by IR and NMR.

EXAMPLE 4

Preparation of (Z)-cis and trans-2-(β-cyyanostyryl)-3-methylcyclopropanecarboxylic acid A solution of sodium ethoxide is prepared by adding sodium spheres (1.15 g, 0.05 mole) to absolute ethanol (100 ml) with stirring until a solution is obtained. Phenylacetonitrile (5.86 g, 0.05 mole) and 2-formyl-3-methylcyclopropanecarboxylic acid methyl ester (7.81 g, 0.05 mole) are added to the above solution at room temperature. The resultant clear solution is stirred for 18 hours at room temperature, then heated at reflux for about 0.5 hours. The reaction mixture is then cooled, evaporated in vacuo, and the residue dissolved in water. The aqueous solution is extracted (3×) with ether and is then acidified with concentrated hydrochloric acid. A brown solid precipitates and is isolated by filtration and dried to afford 8.78 g (77.3%) of a tacky brown solid. NMR data supports the presence of both isomers (the olefin protons of the two isomers appearing as doublets at 6.17 ppm and 6.96 ppm).

EXAMPLE 5

Preparation of (Z)-trans-3-(β-cyanostyryl)-2,2-dimethylcyclopropanecarboxylic acid m-phenoxybenzyl ester A mixture of (Z)-cis and trans-3-(β-cyanostyryl)-2,2-dimethyl-cyclopropanecarboxylic acid (3.5 g), benzene (50 ml), and thionyl chloride (3.4 g) is refluxed for 1 hour. The benzene and excess thionyl chloride are then removed in vacuo. The residue is dissolved in benzene and added to a solution of m-phenoxybenzyl alcohol (2.9 g) in a mixture of benzene (50 ml) and pyridine (1.1 g). The reaction mixture is stirred at room temperature for 3 hours, and then filtered. The filltrate is evaporated in vacuo. The residue is chromatographed on a silica gel column, and eluted with ethyl acetate and hexane to afford the title product.

Analysis calculated for $C_{28}H_{25}O_3N$: C 79.41; H 5.95; N 3.31; Found: C 78.51; H 6.41; N 2.84.

By the above procedure, a number of cyclopropanecarboxylic acid esters are prepared. These are listed in Table II below, together with the corresponding analytical data.

TABLE II

| $R_1$ | $R_2$ | Analysis Calculated | Found |
|---|---|---|---|
| 2-thienyl | CMPB | — | —* |
| 3-Cl-phenyl | MPB | C 73.58<br>H 5.25<br>N 3.04 | C 72.34<br>H 5.65<br>N 2.86 |
| 3-Cl-phenyl | CMPB | C 72.12<br>H 4.80<br>N 5.80 | C 71.47<br>H 5.10<br>N 5.42 |
| 3,4-methylenedioxyphenyl | MPB | C 74.50<br>H 5.39<br>N 3.00 | C 73.25<br>H 5.48<br>N 2.85 |

TABLE II-continued

| R₁ | R₂ | Analysis Calculated | Found |
|---|---|---|---|
| 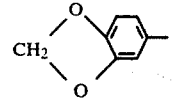 | CMPB | C 73.16<br>H 4.91<br>N 5.69 | C 71.59<br>H 5.22<br>N 5.33 |
| 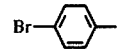 | MPB | C 66.93<br>H 4.81<br>N 2.79 | C 66.33<br>H 4.97<br>N 2.64 |
| 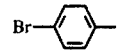 | CMPB | C 66.04<br>H 4.40<br>N 5.31 | C 65.58<br>H 4.74<br>N 4.95 |
| 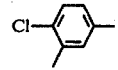 | MPB | C 68.30<br>H 4.71<br>N 2.85 | C 68.60<br>H 4.84<br>N 2.58 |
| 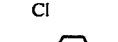 | CMPB | C 67.32<br>H 4.29<br>N 5.42 | C 66.55<br>H 4.64<br>N 5.13 |
| 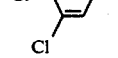 | MPB | C 73.44<br>H 5.28<br>N 3.06 | C 73.12<br>H 5.25<br>N 2.71 |
| 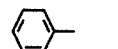 | CMPB | C 72.12<br>H 4.80<br>N 5.80 | C 70.85<br>H 5.03<br>N 5.22 |
| 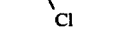 | MPB | C 68.30<br>H 4.71<br>N 2.85 | C 67.83<br>H 4.98<br>N 2.59 |
| 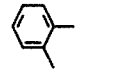 | CMPB | C 67.32<br>H 4.29<br>N 5.41 | C 65.13<br>H 4.11<br>N 5.14 |
| 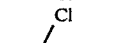 trans | MPB | C 76.17<br>H 5.48<br>N 2.86 | C 75.29<br>H 5.63<br>N 2.86 |
| 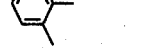 cis | MPB | C 76.17<br>H 5.48<br>N 2.86 | C 76.52<br>H 5.61<br>N 2.69 |
| 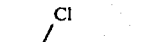 | CMPB | C 74.67<br>H 4.97<br>N 6.00 | C 74.64<br>H 5.15<br>N 5.90 |
| 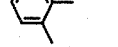 trans | MPB | C 79.61<br>H 6.22<br>N 3.20 | C 79.39<br>H 6.44<br>N 3.01 |
| 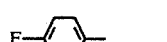 cis | MPB | C 79.61<br>H 6.22<br>N 3.20 | C 79.33<br>H 6.22<br>N 2.85 |
|  | CMPB | C 77.90<br>H 5.67<br>N 6.06 | C 74.54<br>H 5.36<br>N 5.63 |
| 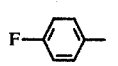 | 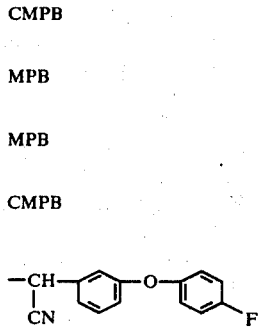 | C 74.67<br>H 4.97<br>N 6.00 | C 74.32<br>H 5.11<br>N 5.55 |
| 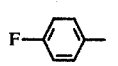 | 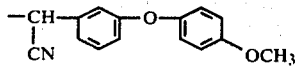 | C 75.30<br>H 5.48<br>N 5.85 | C 74.02<br>H 5.49<br>N 5.84 |
| 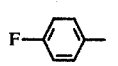 | 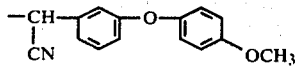 | C 72.11<br>H 4.80<br>N 5.80 | C 72.43<br>H 4.97<br>N 5.53 |

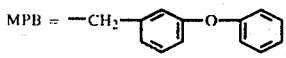

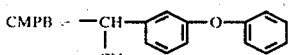

* = NMR doublet 6.27 δ

EXAMPLE 6

Preparation of (Z)-cis and trans-2-(β-cyanostyryl)-3-methylcyclopropanecarboxylic acid, α-cyano-m-phenoxybenzyl ester By the procedure of Example 5, (Z)-cis and trans-2-(β-cyanostyryl)-3-methylcyclopropanecarboxylic acid (5.0 g, 0.022 mole) is reacted with thionyl chloride (d=1.63; 1.75 ml, 0.024 mole), and when formation of the acid chloride is complete, it (the acid chloride) is further reacted with a mixture of α-cyano-m-phenoxybenzyl alcohol (4.5 g, 0.02 mole) and pyridine (1.74 g, 0.022 mole) to yield a crude, gummy product. The crude is purified by dry column chromatography (silica gel; 1:1 methylene chloride/hexane) to give 4.8 g (57.1%) of a yellow gum.

Analysis calculated for $C_{28}H_{22}N_2O_3$: C 77.40; H 5.10; N 6.45; Found: C 76.30; H 5.23; N 6.24.

EXAMPLE 7

Preparation of (Z)-cis and trans 3-(β-cyano-p-methylstyryl)-2,2-dimethyl-cyclopropanecarboxylic acid, m-phenoxybenzyl ester m-Phenoxybenzylbromide (3.68 g; 0.014 mole) is added to a solution of 3-(β-cyano-p-methylstyryl)-2,2-dimethyl-cyclopropanecarboxylic acid (3.19 g; 0.0125 mole) and triethylamine (1.27 g; 0.0125 mole) in dry dimethylformamide and the reaction mixture stirred for 18 hours at room temperature. The reaction mixture, containing some precipitated salts, is poured into water and extracted with ether (2×75 ml). The combined ether extracts are washed several times with water, then with sodium bicarbonate solution and saturated sodium chloride solution. Evaporation of the ether solution yields 3.42 g (62.5%) of a yellow oil. Purification of this yellow oil by dry column chromatography (silica gel; eluent: 1:1 methylene chloride:hexane) affords 0.96 of the trans isomer and 0.6 of the cis isomer.

Analysis calculated for $C_{29}H_{27}NO_3$: C 79.61; H 6.22; N 3.20; (trans) found: C 79.39; H 6.44; N 3.01; (cis) found: C 79.33; H 6.53; N 2.85.

EXAMPLE 8

Preparation of (Z)-cis and trans 3-(β-cyanostyryl)-2,2-dimethyl-cyclopropanecarboxylic acid α-cyano-m-(p-chlorophenoxy)benzyl ester by a phase transfer catalyst esterification process Thionyl chloride (1.61 ml, 2.6 g; 0.022 mole), 3-(β-cyanostyryl)-2,2-dimethyl-cyclopropanecarboxylic acid (4.82 g; 0.02 mole) and toluene are mixed and heated at 100° C. for 1 hour. The reaction mixture is cooled to 25° C. and a solution of m-(p-chlorophenoxy)-benzaldehyde (4.65 g; 0.02 mole) and 18-crown-6 (0.49 g; 0.002 mole) in toluene (10 ml) is added. To this reaction mixture a solution of potassium cyanide (2.6 g; 0.04 mole) in water (6 ml) is added slowly while maintaining the temperature between 20°–25° C. The reaction mixture is then stirred for 18 hours at room temperature. The resultant black reaction mixture is poured in water and extracted with ether (3X). The combined ether extracts are washed with water, 10% hydrochloric acid, 10% sodium bicarbonate, water and saturated sodium chloride solution. The ether layer is dried over sodium sulfate and evaporated in vacuo to leave a brown gum. This gum is purified by dry column chromatography (silica gel; eluent: 1:1 methylene chloride:- hexane) to afford the title product, a yellow glass (1.0 g, 8.6%).

Analysis calculated for $C_{29}H_{23}ClN_2O_3$: C 72.12; H 4.80; N 5.80; Found: C 72.43; H 4.97; N 5.53.

EXAMPLE 9

Preparation of 20% w/w emulsifiable concentrates containing cyanovinyl pyrethroids of the invention

Toxicants 1. (Z)-3-(p-chloro-β-cyanostyryl)-2,2-dimethylcyclopropanecarboxylic acid, α-cyano-m-phenoxybenzyl ester.
2. (Z)-trans-3-(β-cyanostyryl)-2,2-dimethylcyclopropanecarboxylic acid, α-cyano-m-phenoxybenzyl ester.
3. (Z)-trans-3-(2,4-dichloro-β-cyanostyryl)-2,2-dimethylcyclopropanecarboxylic acid, α-cyano-m-phenoxybenzyl ester.

| Component | Concentrates wt. in g. |
|---|---|
| Toxicant | 15.0 |
| Atlox ® 3403F/3404F; 50:50 mixture[a] | 10.125 |
| xylene | 6.75 |
| "HAN"[b] | 35.625 |
| Total: | 67.500 |

(a) Atlox ® 3403F, a polyoxyethylene alkyl aryl ether-alkyl aryl sulfonate blend; nonionic surfactant; specific gravity: 1.02 at 20° C.; wt in kg/1=1.018 (8.5 lb/gal); approximate viscosity at 25° C.=130 cps; flash point (C.O.C.; °F.)=100.

Atlox ® 3404F a polyoxyethylene ether polyoxyethylene glyceride-alkyl aryl sulfonate blend; anionic surfactant; specific gravity 1.05 at 25° C.; wt in kg/1=1.042 (8.7 lb/gal); approximate viscosity at 25° C.=3700 cps; flash point (C.O.C.; °F.)=160. Both are proprietary products of ICI United States Inc. Atlas Chemicals Division, Wilmington, Del.

(b) "HAN"=Heavy Aromatic Naphta, boiling range 165° C. to 282° C.; mixed aniline point °C.=28.0; freeze point °C.=−36; aromatic content:80%.

Method of preparation.

The toxicant is preheated to about >85° C. to obtain a flowable melt, and then mixed with the surfactants, xylene and "HAN". The resultant mixture is heated and stirred to obtain a clear solution.

Standard emulsification test (50λ/33 ml) medium hard water) indicates, that although on addition the emulsifiable concentrate tends to float on top of the water layer, with agitation (or shaking) good emulsions are obtained, which remain quite stable with very little creaming on top.

The average micelle sizes of the aqueous emulsions prepared from the above concentrates are determined using a Coulter Counter with the following results:

| Emulsion Containing Toxicant No. | Micelle size in microns |
|---|---|
| 1 | 4.5 |
| 2 | 2.2 |
| 3 | 2.4 |

EXAMPLE 10

Evaluation of the efficacy of the compounds of the invention for the control of *Boophilus microplus* larvae Effective control of acarina larvae is demonstrated in the following tests with larvae of *Boophilus microplus*, a one-host tick which can remain on a single host through its three life stages, i.e. larva, nymph and adult. In these tests a 10% acetone/90% water mixture contains the test compound at the concentrations indicated in Table III below. Twenty larvae are enclosed in a pipet sealed at one end with a gauze material, and a solution, containing the test compound at the concentrations given, is then drawn through the pipet with a vacuum hose simulating a spray system. The ticks are then held for 48 hours at room temperature, and percent mortality rates are then determined. The results obtained with the various compounds are tabulated in Table III below.

EXAMPLE 11

Suppression of fecundity and chemosterilant effect in Ixodidae

The efficacy of the compounds of the invention for suppression of fecundity and chemosterilant effect in ticks is demonstrated in the following tests wherein engorged adult female *Boophilus microplus*, multiple resistant strain, ticks which have dropped from cattle are collected and used for testing.

The compound to be tested is dissolved in a 35% acetone/65% water mixture in amounts sufficient to provide the concentrations indicated in Table IV below. Ten ticks per treatment are used and they are immersed in the test solution for three to 5 minutes, then removed and held in incubators for two to three weeks at 28° C. Counts of ticks laying eggs are then made and recorded. Eggs which were laid are placed in containers and kept for one month to observe hatching and to determine chemosterilant effect. Results of these test are given in Table IV below.

TABLE III

Efficacy of cyanovinyl pyrethroids for control of *Boophilus microplus* larvae.

| $R_1$ | $R_2$ | Concentration of Toxicant in spray solution (ppm) | Percent Mortality of *Boophilus Microplus* larvae. |
|---|---|---|---|
|  | CMPB | 0.001 | 100 |
|  | MPB | 0.001 | 100 |
|  | CMPB | 0.001 | 100 |
|  | MPB | 1.0 | 100 |
|  | CMPB | 1.0 | 100 |
|  | MPB | 0.001 | 100 |
|  | CMPB | 0.001 | 100 |
|  | CMPB | 100.0 | 100 |
| 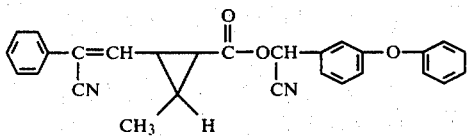 | | 1<br>0.1 | 100<br>50 |

MPB = 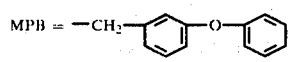

CMPB = 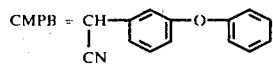

TABLE IV

Efficacy of cyanovinyl pyrethroids expressed as % reduction of viable egg masses.

$$R_1-\underset{CN}{C}=CH-\underset{\underset{CH_3}{\diagup}\underset{CH_3}{\diagdown}}{\triangle}-\overset{O}{\underset{\|}{C}}-O-R_2$$

| R₁ | R₂ | Concentration in solution (ppm) | Percent reduction of viable egg masses |
|---|---|---|---|
|  | CMPB | 31.2<br>16.0<br>8.0<br>8.0<br>4.0 | 95.9–99<br>85<br>65<br>84–94<br>62–70 |
| 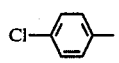 | MPB | 15<br>8<br>4 | 99.4<br>72.9–78<br>24.5–32 |
| 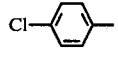 | CMPB | 4<br>2 | 99.4<br>97 |
| 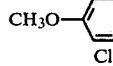 | MPB | 250<br>125<br>62<br>31 | 85.5–87.8<br>79.1–91.2<br>90.9–96.6<br>63.6 |
| 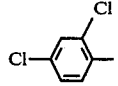 | CMPB | 31<br>15 | 91.8<br>73.5 |
| 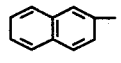 | MPB | 32<br>16<br>8 | 85.6–91<br>87.5–95<br>40–64 |
| 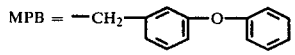 | CMPB | 4<br>2 | 97<br>55 |
| 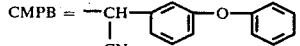 | CMPB | 15 | 92 |
| 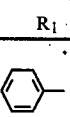 | CMPB | 100 | 100 |
|  | CMPB | 31 | 98.8 |

MPB = $-CH_2-$

CMPB = $-\underset{CN}{CH}-$

EXAMPLE 12

Evaluation of the efficacy of cyanovinyl pyrethroids for the control of *Boophilus microplus* on cattle Test compounds The 20% w/w emulsifiable concentrates of Example 6 are used in this experiment. Spray emulsions are prepared just prior to use from the above concentrates by diluting 11.25 ml and 22.5 ml of each with 75 liter of water to yield spray emulsions containing 30 and 60 ppm of active ingredient, respectively.

Test animals

Holstein calves, 6 to 12 months old are experimently infested with about 5000 larval ticks of a multiple resistant (resistant to organophosphate acaricides as well as to toxaphene and lindane) strain placed on each animal three times a week, starting 35 days pre-treatment. Three pre-treatment tick counts are made in days —6, —5 and —4. Calves are allocated to groups of five on the basis of these counts. One group serves as infected nontreated controls and one group each is used to evaluate the test compounds at 30 and 60 ppm level of toxicant, respectively.

On treatment day, each animal is sprayed with a total of 15 liters of emulsion delivered at 21.09 kg/cm² pressure with a "Teejet 8002 Excelsior" nozzle providing a fan-shaped spray. Mortality counts (female ticks 4.5–8.0 mm) are taken over days 2 to 21 posttreatment for a total of 9 times. Residual effect is measured by six mortality counts taken over days 23 to 35 posttreatment. The results obtained, are summarized and tabulated in Table V below.

TABLE V

Evaluation of the efficacy of the compounds of the present invention for the control of multiple resistant ticks on cattle.

$$R_1-\underset{CN}{C}=CH-\underset{\underset{CH_3}{\diagup}\underset{CH_3}{\diagdown}}{\triangle}-\overset{O}{\underset{\|}{C}}-O-\underset{CN}{CH}-\underset{}{\bigcirc}-O-\bigcirc$$

| R₁ | Toxicant Concentration (ppm) | Percent Mortality (post-treatment) Days 2 to 21 | Days 23 to 35 |
|---|---|---|---|
|  | 30<br>60 | 95.8<br>99.2 | 97.8<br>99.4 |
| 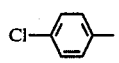 | 30<br>60 | 92.9<br>96.8 | 99.2<br>99.2 |
| 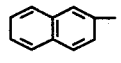 | 30<br>60 | 65<br>85.9 | 89.2<br>95.5 |

EXAMPLE 13

Evaluation of the Ixodicidal activity of cyanovinyl pyrethroids against *Amblyomma hebreum* in vitro The ixodicidal activity of the compounds of the invention is demonstrated in the following tests wherein juvenile adult *Amblyomma hebreum* ticks are collected and used for testing.

The compound to be tested is dissolved in a 35% acetone/65% water mixture in amounts sufficient to provide the concentrations indicated in Table VI below. Ten ticks per treatment (ten males or ten females) are used and they are immersed in the test solution for three to 5 minutes, then removed and held in incubators at 28° C. Percent mortality is determined at 24 and 96 hours post-immersion. The data obtained are tabulated in Table VI below.

TABLE VI

Percent Mortality of *Amblyomma hebreum* at 24 hours post-immersion.

$$R_1-\underset{CN}{C}=CH-\overset{CH_3\ CH_3}{\triangle}-\overset{O}{\underset{\|}{C}}-O-\underset{CN}{CH}-\phenyl-O-\phenyl$$

| $R_1$ | Concentration of Toxicant (ppm) | % Mortality at 24 hours | Remarks |
|---|---|---|---|
| phenyl | 240 | 100 | |
| | 120 | 100 | |
| | 60 | 90 | 100% at 96 hours |
| | 30 | 45 | 75% at 96 hours |
| | 15 | 6 | |
| | 7.5 | 15 | |
| | 3.25 | 0 | |
| 4-Cl-phenyl | 240 | 95 | |
| | 120 | 70 | |
| | 60 | 45 | |
| | 30 | 75 | |
| | 15 | 15 | |
| | 7.5 | 0 | |
| | 3.25 | 0 | |
| 2,4-Cl₂-phenyl | 240 | 100 | |
| | 120 | 100 | |
| | 60 | 65 | |
| | 30 | 60 | |
| | 15 | 50 | |
| | 7.5 | 0 | |
| | 3.25 | 0 | |

EXAMPLE 14

Evaluation of the efficacy of the compounds of the invention for the control of face flies (*Musca autumnalis*)

The cyanovinyl pyrethroids in these tests are dissolved in acetone to afford stock solutions at a concentration of 1000 ppm each.

One kg of fresh, untreated cow manure and the appropriate volume of the stock solution of the pyrethroid used in the test are mixed for two minutes with a Hobart heavy duty mixer to yield a blend containing the toxicant at the ppm concentration indicated in Table VII below. Control samples are prepared similarly using the corresponding volumes of acetone (no toxicant). Two 148 cm² (5-oz) plastic dixie cups are then mounded full of treated or untreated manure. A small reservoir is made in the top of the manure, and into this reservoir are placed twenty two-day old *Musca autumnalis* larvae. The larvae are then covered with the same manure. Each cup is placed in an individual sand tray for pupation, and maintained for 5 days. At the end of this period mortality counts are made. The results are given in Table VII below.

TABLE VII

In vitro activity of cyanovinyl pyrethroids for the control of *Musca autumnalis*.

$$R_1-\underset{CN}{C}=CH-\overset{CH_3\ CH_3}{\triangle}-\overset{O}{\underset{\|}{C}}-O-R_2$$

| $R_1$ | $R_2$ | Concentration (ppm) | Percent Mortality of *Musca autumnalis* |
|---|---|---|---|
| phenyl | CMPB | 1 | 100 |
| | | 0.1 | 83 |
| phenyl | MPB | 10 | 100 |
| 4-Cl-phenyl | MPB | 10 | 100 |
| 4-Cl-phenyl | CMPB | 1 | 83 |
| | | 0.1 | 100 |
| 4-CH₃O-phenyl | MPB | 10 | 70.8 |
| 4-CH₃O-phenyl | CMPB | 10 | 100 |
| 2,4-Cl₂-phenyl | MPB | 10 | 100 |
| 2,4-Cl₂-phenyl | CMPB | 10 | 94.7 |

$$MPB = -CH_2-\phenyl-O-\phenyl$$

$$CMPB = -\underset{CN}{CH}-\phenyl-O-\phenyl$$

EXAMPLE 15

Evaluation of cyanovinyl pyrethroids for the control of Screwworm fly (*Cochliomyia hominivorax*) larvae.

Screwworm Larvae

Newly hatched larvae are obtained after incubation of 100–120 mg egg masses placed on filter paper, wetted with isotonic saline solutions in petri dishes, and kept at 27° C. and 80%–90% RH for 12–15 hours. The hatched larvae are reared on the following medium and maintained at 37° C.:

| Lean ground beef | 57.00 g |
|---|---|
| Bovine plasma | 21.4 ml |
| Water | 21.3 ml |
| Formalin | 0.3 ml |
| Total: | 100.0 |

After 48 hours, larvae are transferred to trays containing a slightly different medium and maintained in a water bath at 39°–40° C.:

| Lean ground beef | 40.0 g |
|---|---|
| Citrated bovine blood | 20.0 ml |
| Water | 39.7 ml |
| Formalin | 0.3 ml |
| Total: | 100.0 |

Two ml of an acetone-water solution, containing 10 times the final desired concentration of toxicant, is mixed with 18 g of nutritional medium in a 60 ml jar. The mixture is kept in a water bath at 39°-40° C. for about 30 minutes, i.e., until the medium reaches the same temperature. Then masses of 200-300 newly hatched screwworm larvae added to each jar containing the toxicant mixed with the nutritional medium. Larvae are picked up with a cardboard spatula from the petri dish where they had been incubated. Special care is taken to place larval masses over an "island" in the plasma medium. A new spatula is used for each concentration of toxicant. The jars are covered with a piece of muslin and kept in a water bath at 40° C. to the end of the experiment. Two replicates are used per concentration. Controls containing no toxicant but the highest concentration of acetone in the nutrient medium are kept for each experiment.

Final check, by visual inspection is made on the surface of the media after 48 hours, and the approximate percent mortality determined.

The results obtained are averaged and tabulated in Table VIII below.

TABLE VIII
Efficacy of Cyanovinyl pyrethroids expressed as percent mortality of Screwworm Fly larvae.

$$R_1-\underset{CN}{C}=CH-\underset{CH_3\;\;CH_3}{\triangle}-\underset{O}{\overset{\|}{C}}-OR_2$$

| $R_1$ | $R_2$ | Concentration of Toxicant (ppm) | Percent Mortality of Screwworm Fly larvae (approximate) |
|---|---|---|---|
| phenyl | CMPB | 25 | 100 |
|  |  | 5 | 21.1 |
| phenyl | MPB | 25 | 34.1 |
| 4-Cl-phenyl | CMPB | 25 | 90 |
|  |  | 5 | 7 |
| 2,4-diCl-phenyl | CMPB | 25 | 7.3 |

MPB = $-CH_2-\phenyl-O-\phenyl$

CMPB = $-\underset{CN}{CH}-\phenyl-O-\phenyl$

EXAMPLE 13
Evaluation of the siphonaptericidal activity of cyanovinyl pyrethroids The siphonaptericidal activity of the compounds of this invention is demonstrated by the following tests wherein the cyanovinyl pyrethroids listed in Table IX below are utilized as the active ingredients. In these tests, ten adult fleas of the species *Ctenocephalides felis* are sprayed for 30 seconds with an acetone/water solution containing 50 and 10 ppm of the test compound, respectively. After this treatment, the fleas are maintained for 48 hours at room temperature and 80+% relative humidity. At the end of this period the fleas are examined and mortality counts made. The results are tabulated in Table IX below.

TABLE IX
Activity of cyanovinyl pyrethroids against *Ctenocephalides felis*

$$R_1-\underset{CN}{C}=CH-\underset{CH_3\;\;CH_3}{\triangle}-\overset{O}{\overset{\|}{C}}-O-\underset{CN}{CH}-\phenyl-O-\phenyl$$

| $R_1$ | Concentration of Toxicant (ppm) | Percent Mortality of *Ctenocephalides felis* |
|---|---|---|
| phenyl | 50 | 100 |
|  | 10 | 45 |
| 4-Cl-phenyl | 50 | 100 |
|  | 10 | 100 |
| 2,4-diCl-phenyl | 50 | 90 |
|  | 10 | 100 |

EXAMPLE 17
Insecticide testing procedures

Malaria Mosquito (*Anopheles quadrimaculatus* Say) egg and larvae test

One ml of a 300 ppm solution is pipetted into a 400 ml beaker containing 250 ml of deionized water and stirred with the pipette, giving a concentration of 1.2 ppm. A wax paper ring 0.6 cm wide to fit inside the beaker is floated on the surface of the test solution to keep the eggs from floating up the meniscus curve and drying out on the side of the glass. A spoon made of screen is used to scoop up and transfer about 100 eggs (0–24 hours old) into the test beaker. After two days at 26.7° C. observations of hatching are made. This includes kill of eggs or inhibition of hatch, kill of newly hatched larvae, or delayed hatch. Additional observations are made after another day for the same effects.

Tobacco Budworm [*Heliothis virescens* (Fabricius)]

A cotton plant with 2 true leaves expanded is dripped for 3 seconds with agitation in a 300 ppm solution. A 1.25 to 2 cm square of cheesecloth with about 50 to 100 budworm eggs 0–24 hours old is also dipped in the test solution and placed on a leaf of the cotton plant, all being placed in a hood to dry. The leaf with the treated budworm eggs is removed from the plant and placed in a 236.6 ml (8-oz) Dixie cup with a wet 5 cm piece of dental wick and covered with a lid. The other leaf is placed in a similar cup with a wick and a piece of cheesecloth infested with 50–100 newly hatched larvae is added before covering the cup with a lid. After 3 days at 26.7° C., observations of egg hatch made as well as kill of newly hatched larvae, any inhibition of feeding, or interference of any sort with normal development.

Phosphate Resistant Strain of Two-Spotted Spider Mite [*Tetranychus urticae* (Koch)]

Sieva lima bean plants, with primary leaves 7.6 to 10 cm long, are infested with about 100 adult mites per leaf 4 hours before use in this test, in order to allow egglaying before treatment. The infested plants are dipped for 3 seconds with agitation into a 300 ppm solution, and the plants set in the hood to dry. After 2 days at 26.7° C.

the adult mite mortality is estimated on one leaf under a 10× stereoscopic microscope. The other leaf is left on the plant an additional 5 days and then examined at 10× power to estimate the kill of eggs and newly-hatched nymphs, giving a measure of ovicidal and residual action, respectively.

Southern Armyworm [*Spodoptera eridania* (Cramer)]

A Sieva lima bean plant with just the primary leaves expanded to 7.6 cm to 10 cm is dipped for 3 seconds with agitation in a 1000 ppm solution and set in a hood to dry. Following this, one leaf is placed in a 10 cm petri dish which has a moist filter paper in the bottom and 10 third-instar armyworn larvae about 1 cm long. The dish is covered and held at 26.7° C. After 2 days mortality counts and estimates of the amount of feeding are made. Compounds showing partial kill and/or inhibition of feeding are held for an extra day for further observations.

All compounds showing activity as defined above are retested, using the second leaf on the bean plant, after an interval of 7 days from original treatment, as an assay of residual activity.

Mexican Bean Beetle (*Epilachna varivestis* Mulsant)

Sieva lima bean plants (2 per pot) with primary leaves 7.6 to 10 cm long, are dipped in a 300 ppm solution and set in a hood to dry. One leaf is removed from the plant and placed in a 10 cm petri dish containing a moist filter paper on the bottom and 10 last-instar larvae (13 days from hatching).

The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Western Potato Leaf Hopper (*Empoasca abrupta* DeLong)

A lima bean plant with the primary leaf expanded to 7.6 to 10 cm is dipped into a 100 ppm solution and set in a hood to dry. A 2.5 cm piece of the tip of 1 leaf is cut off and placed in a 10 cm petri dish with a moist filter paper in the bottom. (In practice, this is usually cut off the tip of a plant from the Mexican bean beetle tests using a bean leaf dipped in the needed solution). From 3 to 10 second-instar nymphs are tapped from the culture plants into the test dish and rapidly covered. Mortality counts are made after two days at 26.7° C.

Malaria Mosquito (*Anopheles quadrimaculatus* Say) Adult Test

Ten ppm solutions are poured into wide-mouth 56 g jars each containing a microscope slide. The slides are removed from the test solution with forceps and laid horizontally to dry on a wide-mouth 112 g bottle. When dry, they are placed in the same 112 g bottle and ten 4 to 5-day old mosquitoes of mixed sexes are added to each bottle. A pieces of cotton gauze held on by an elastic band serves as a lid and a wad of cotton soaked in 10% honey solution serves as food. Mortality counts are made after 1 day at 26.7° C.

Bean Aphid (*Aphid fabae* Scopoli)

Five cm fiber pots, each containing a nasturtium plant 5 cm high and infested with 100 to 500 aphids 2 days earlier are placed on a 4 rpm turntable and sprayed with a 100 ppm solution for 2 revolutions with a No. 154 De Vilbiss atomizer at 1.4 kg/cm$^2$ air pressure. The spray tip is held about 15 cm from the plants and the spray directed so as to give complete coverage of the aphids and the plants. The sprayed plants are laid on their sides on white enamel trays. Mortality estimates are made after 1 day at 26.7° C.

Tobacco Budworm [*Heliothis virescens* (Fabricisus)]

Third instar

Three cotton plants with just expanded cotyledons are dipped in a 1000 ppm solution, and placed in a hood to dry. When dry, each cotyledon is cut in half and 10 are each placed in a 28 g plastic medicine cup containing a 1.25 cm dental wick saturated with water, and one third-instar budworm larva is added. The cup is capped and held for 3 days at 26.7° C., after which mortality counts are made.

Cabbage Looper [*Trichoplusia ni* (Hubner)]

A primary leaf of a cotton plant is dipped in the test solution and agitated for 3 seconds. It is then set in a hood to dry. Following this, the leaf is placed in a 10 cm petri dish containing a moist filter paper at the bottom and 10 third-instar loopers. The dish is covered and held at 26.7° C. After 2 days, mortality counts and estimates of feeding damage are recorded. Those materials showing partial kill and/or inhibition of feeding are held for another day for further observations.

Compounds rated active (8 or 9) are further tested at reduced concentrations in 50% acetone:50% water.

The rating system employed in these tests is as follows:

| Rating System |
| --- |
| 0 = 0–40% killed or affected |
| 1 = reduced feeding (trace to light damage) |
| 2 = some deformed insects (40–80%) |
| 3 = mostly deformed insects (85%–100%) |
| 4 = not an index number at present |
| 5 = 41–60% mortality |
| 6 = 61–70% mortality |
| 7 = 71–85% mortality |
| 8 = 86–95% mortality |
| 9 = 100% mortality |

The absence of a number indicates that no test has been run at that particular dosage.

Data obtained are reported in Table X below.

TABLE Xa

Insecticide evaluation.

$$R_1-C(CN)=CH-\text{cyclopropyl}(CH_3)(CH_3)-C(=O)-OR_2$$

| | | Mosquito Larvae ppm | | | Tobacco Budworm Eggs (ppm) | | | Tobacco Budworm Larvae (ppm) | | |
|---|---|---|---|---|---|---|---|---|---|---|
| R₁ | R₂ | 1.2 | 0.4 | 0.04 | 300 | 100 | 10 | 300 | 100 | 10 |
| phenyl | CMPB | 9 | 9 | 9 | 8 | 0 | | 9 | 9 | 0 |
| phenyl | MPB | 9 | 9 | 0 | 8 | 0 | | 9 | 8 | 0 |
| 4-Cl-phenyl | MPB | 8 | 6 | 0 | 0 | | | 9 | 9 | 0 |
| 4-Cl-phenyl | CMPB | 9 | 9 | 0 | | | | 9 | 9 | 5 |
| 2-thienyl | CMPB | 9 | 9 | 9 | 8 | 0 | | 7 | 0 | |

MPB = 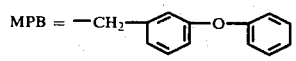

CMPB = 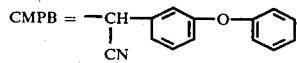

TABLE Xb $$R_1-C(CN)=CH-\text{cyclopropyl}(CH_3)(CH_3)-C(=O)-OR_2$$

| | | 2-Spotted Spider Mites ppm | | Southern Armyworms ppm | | | Mexican Bean Beetle ppm | | |
|---|---|---|---|---|---|---|---|---|---|
| R₁ | R₂ | 300 | 100 | 1000 | 100 | 10 | 300 | 100 | 10 |
| phenyl | CMPB | 9 | 0 | 9 | 9 | 0 | | | |
| phenyl | MPB | 9 | 0 | 9 | 0 | | | | |
| 4-Cl-phenyl | CMPB | 9 | 0 | 1 | 0 | | 9 | 8 | 0 |
| 4-CH₃O-phenyl | CMPB | 0 | | 0 | | | 9 | | |
| 2-thienyl | CMPB | 0 | | 9 | 5 | 0 | 9 | 9 | 0 |

MPB = 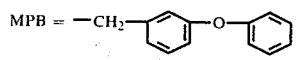

CMPB = 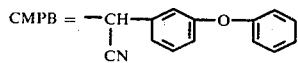

TABLE Xc $$R_1-\underset{\underset{CN}{|}}{C}=CH-\overset{\overset{CH_3\ CH_3}{\triangle}}{}\overset{O}{\underset{}{\|}}C-O-R_2$$

| R₁ | R₂ | Leaf Hopper (ppm) | | | Mosquito (ppm) | | Bean Aphids (ppm) | | | Tobacco Budworm (ppm) | | Cabbage* Looper (ppm) | |
|---|---|---|---|---|---|---|---|---|---|---|---|---|---|
| | | 100 | 10 | 1 | 10 | 1 | 100 | 10 | 1 | 1000 | 100 | 1000 | 100 |
| phenyl | CMPB | 9 | 7 | 7 | 0 | | 9 | 6 | 0 | 6 | 7 | 9 | 5 |
| phenyl | MPB | 9 | 7 | 7 | 0 | | 9 | 7 | 0 | 8 | 0 | 0 | 0 |
| Cl-phenyl (p) | MPB | 9 | 0 | 5 | 0 | | 9 | 8 | 0 | 5 | 0 | 9 | 1 |
| Cl-phenyl (p) | CMPB | 9 | 5 | 5 | 0 | | 9 | 9 | 9 | 8 | 1 | 9 | 9 |
| CH₃O-phenyl (p) | MPB | 5 | 0 | 0 | | | 9 | 5 | | 5 | 0 | 5 | 0 |

TABLE Xc $$R_1-\underset{\underset{CN}{|}}{C}=CH-\overset{\overset{CH_3\ CH_3}{\triangle}}{}\overset{O}{\underset{}{\|}}C-O-R_2$$

| R₁ | R₂ | Leaf Hopper (ppm) | | | Mosquito (ppm) | | Bean Aphids (ppm) | | | Tobacco Budworm (ppm) | | Cabbage* Looper (ppm) | |
|---|---|---|---|---|---|---|---|---|---|---|---|---|---|
| | | 100 | 10 | 1 | 10 | 1 | 100 | 10 | 1 | 1000 | 100 | 1000 | 100 |
| CH₃O-phenyl (p) | CMPB | 7 | 0 | 0 | | | 9 | 6 | 0 | | 0 | | 0 |
| 2,4-dichlorophenyl | CMPB | 9 | 7 | 0 | | | 9 | 8 | 0 | | 0 | — | |
| naphthyl | CMPB | 7 | | 0 | | | 8 | 0 | | 1 | | 0 | |
| thienyl | CMPB | 7 | | 0 | | | 7 | 0 | | | | 9 | 9 |

MPB = —CH₂—C₆H₄—O—C₆H₅

CMPB = —CH(CN)—C₆H₄—O—C₆H₅

* = 3rd Instar

I claim:

1. A compound of the formula:

$$R_1-\underset{\underset{CN}{|}}{C}=CH-\overset{\overset{CH_3\ R_2}{\triangle}}{}\overset{O}{\underset{}{\|}}C-OH$$

wherein R₁ is

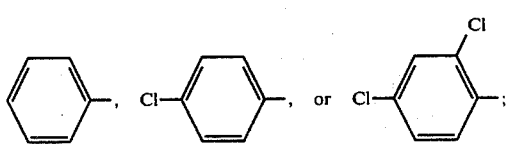

and R₂ is methyl.

2. A compound according to claim 1, (Z)-cis and trans-3-(β-cyanostyryl)-2,2-dimethyl-cyclopropanecarboxylic acid.

3. A compound according to claim 1, (Z)-cis and trans-3-(p-chloro-β-cyanostyryl)-2,2-dimethyl-cyclopropanecarboxylic acid.

4. A compound according to claim 1, (Z)-cis and trans-3-(2,4-dichloro-β-cyanostyryl)-2,2-dimethyl-cyclopropanecarboxylic acid.

5. A compound according to claim 1, (E)-trans-3-(β-cyanostyryl)-2,2-dimethyl-cyclopropanecarboxylic acid.

6. A method for the preparation of a compound of the formula:

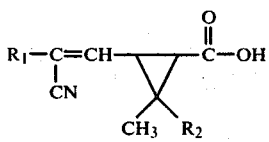

wherein $R_1$ is

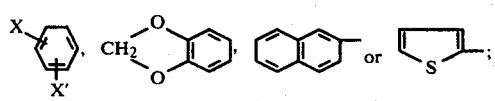

$R_2$ is hydrogen or methyl, X and X' are each hydrogen, halogen, $C_1$-$C_3$ alkyl, $C_1$-$C_3$ alkoxy or haloalkyl $C_1$-$C_2$; the cis and trans cyclopropane isomers, the E and Z side-chain olefin isomers, the optical isomers thereof and the isomeric mixtures thereof; comprising reacting a compound of formula (I):

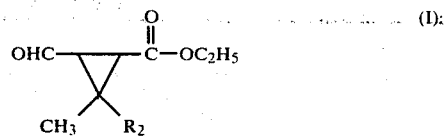

wherein $R_2$ is as hereinabove defined with a compound of formula (II) $R_1$—$CH_2$—CN in the presence of a $C_1$-$C_3$ alcohol and sodium ethoxide at ambient temperature for a period of time sufficient to essentially complete the condensation of the formyl group of the compound of formula (I) with the active methylene group of the compound of formula (II); wherein $R_1$ is as hereinabove defined.

7. A method according to claim 6, wherein $R_1$ is

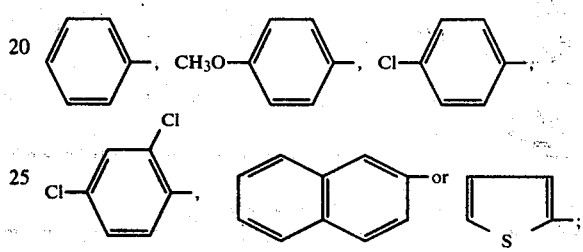

and $R_2$ is methyl.

* * * * *